United States Patent

Hofer et al.

[11] 4,033,957
[45] July 5, 1977

[54] TRIAZINE DERIVATIVES AS STABILIZERS FOR ORGANIC MATERIALS

[75] Inventors: Kurt Hofer, Munchenstein; Guenther Tscheulin, Riehen, both of Switzerland

[73] Assignee: Sandoz Ltd., Basel, Switzerland

[22] Filed: Dec. 3, 1974

[21] Appl. No.: 529,024

[30] Foreign Application Priority Data

Dec. 10, 1973 Switzerland .............. 17269/73

[52] U.S. Cl. .............. 260/246 B; 260/247.1 M; 260/247.2 A; 260/247.2 B; 260/249.5; 260/249.6; 260/249.8; 260/45.8 NT; 260/45.8 NZ
[51] Int. Cl.² .............. C07D 401/14; C07D 413/14; C07D 251/04
[58] Field of Search ..... 260/246 B, 249.6, 247.2 A, 260/249.5, 247.1 M, 247.2 B, 249.8

[56] References Cited

UNITED STATES PATENTS

| | | | |
|---|---|---|---|
| 1,915,334 | 6/1933 | Salzberg et al. | 260/293.51 |
| 2,075,359 | 5/1937 | Salzberg et al. | 260/584 |
| 3,594,374 | 7/1971 | Varsanyi et al. | 260/249.6 |
| 3,925,376 | 12/1975 | Chalmers et al. | 260/249.6 |

Primary Examiner—Raymond V. Rush
Assistant Examiner—Jose Tovar
Attorney, Agent, or Firm—Gerald D. Sharkin; Richard E. Vila; Joseph J. Borovian

[57] ABSTRACT

Triazine derivatives of formula

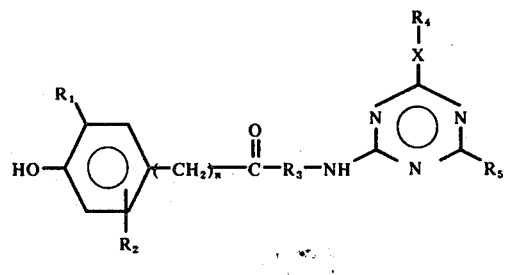

in which
$R_1$ is a tertiary alkyl radical,
$R_2$ is hydrogen or a substituent, e.g. alkyl,
$n$ is 0 or an integer,
$R_3$ is —NH— or —O—$(CH_2)_m$
wherein $m$ is an integer,
X is —O—, —S— or —$NR_6$—,
wherein $R_6$ is hydrogen or a substituent, e.g. alkyl or phenyl,
$R_4$ is one of the radicals signified by $R_6$, or, when X is —NH—, a radical of formula

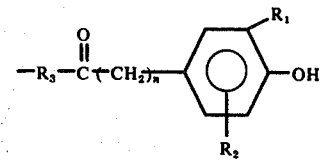

$R_1$, $R_2$, $n$ and $R_3$ being as indicated above,
or $R_4$, $R_6$ and the common nitrogen atom, and optionally a further hetero atom, form a saturated 5- or 6-membered heterocyclic ring,
and $R_5$ is one of the radicals signified by —X—$R_4$, or a substituent, e.g. alkyl, are useful for stabilizing organic materials, e.g. polypropylene, against the degradative effects of oxygen, heat and/or light.

10 Claims, No Drawings

TRIAZINE DERIVATIVES AS STABILIZERS FOR ORGANIC MATERIALS

The present invention relates to organic compounds, more particularly triazine derivatives, and their use in the stabilization of organic materials against the degradative effects of oxygen, heat and/or light.

Accordingly, there are provided compounds, having stabilising effects on organic materials, of formula I,

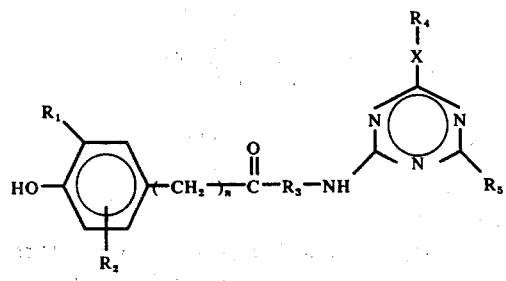

in which
$R_1$ is a $C_{4-9}$ tertiary alkyl radical,
$R_2$ is a hydrogen atom or a $C_{1-18}$ alkyl, $C_{5-12}$ cycloalkyl, $C_{6-12}$ cycloalkylalkyl or $C_{7-12}$ phenylalkyl radical,
$n$ is 0 or an integer 1 to 3,
$R_3$ is —NH— or —O—(CH$_2$)$_m$—,
wherein $m$ is an integer 2 to 4,
X is —O—, —S— or —NR$_6$—,
   wherein $R_6$ is a hydrogen atom or a $C_{1-18}$ alkyl, $C_{5-12}$ cycloalkyl, $C_{6-12}$ cycloalkylalkyl, phenyl or $C_{7-12}$ phenylalkyl radical, of which the phenyl radical and the phenyl radical of the phenylalkyl radical is unsubstituted or substituted with up to 3 substituents selected from 1 to 3 halogen atoms and 1 or 2 hydroxyl, 1 to 3 $C_{1-12}$ alkyl, 1 to 3 $C_{1-18}$ alkoxy, 1 phenyl, 1 benzyl and 1 phenoxy radicals, the aggregate of the carbon atoms in the alkyl radicals and in the alkoxy radicals not exceeding 12 and 18, respectively,
$R_4$ is, independently, one of the radicals signified by $R_6$, or, when X is —NH—, additionally a radical of formula II,

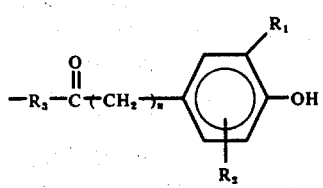

wherein $R_1$, $R_2$, $n$ and $R_3$ are, independently, as defined above,
or $R_4$, together with $R_6$ and the common nitrogen atom and optionally with a further hetero atom, form a saturated 5- or 6-membered heterocyclic ring,
and $R_5$ is, independently, one of radicals signified by —X—$R_4$, or a $C_{1-12}$ alkyl or an unsubstituted phenyl radical, or a phenyl radical substituted with 1 or 2 $C_{1-6}$ alkyl radicals.

In this specification, an "alkyl" radical, so far as the number of carbon atoms permits and unless specified in definite terms, is a natural or synthesisible, straight-or branched-chain primary, secondary or tertiary alkyl radical. By "halogen atom" is meant fluorine, chlorine or bromine. Examples of hetero atoms which may be additional to the nitrogen atom in the radical of formula —NR$_4$R$_6$ (X in the formula I being —NR$_6$—) when this formula signifies a saturated 5- or 6-membered heterocyclic ring are oxygen, sulphur and nitrogen atoms. Examples of heterocyclic rings signified by —NR$_4$R$_6$ are piperidino, piperazino, morpholino, thiomorpholino, pyrrolidino and imidazolidino. Preferably any halogen atom is chlorine.

In the compounds of formula I and in any radical of formula II, $R_1$ is preferably a $C_{4-6}$ tertiary alkyl radical and more preferably a tertiary butyl radical, $R_2$ is preferably an alkyl radical, and $n$ is preferably 0, 1 or 2. $R_4$ in the compounds of formula I is preferably an alkyl, unsubstituted or substituted phenyl or unsubstituted or substituted phenylalkyl radical, a radical of formula II, or forms with —NR$_6$— and optionally with a further hetero atom a saturated 5- or 6-membered heterocyclic ring, and is more preferably an alkyl or unsubstituted or substituted phenyl radical, or forms with —NR$_6$— and optionally with a further hetero atom a saturated 5- or 6-membered heterocyclic ring. $R_6$ is preferably a hydrogen atom, an alkyl, unsubstituted or substituted phenyl or unsubstituted or substituted phenylalkyl radical, or forms with —NR$_4$— and optionally with a further hetero atom a saturated 5- or 6-membered heterocyclic ring, and more preferably a hydrogen atom, an alkyl or unsubstituted or substituted phenyl radical, or forms with —NR$_4$— and optionally with a further hetero atom a saturated 5- or 6-membered heterocyclic ring. The preferred significances of X are —S— and —NR$_6$—, of which —NR$_6$— is the more preferred, and $R_5$ is preferably —X—$R_4$. Preferably the molecule of formula I contains a maximum of 2 radicals of formula II.

When $R_2$ is an alkyl radical, this is preferably $C_{1-8}$ alkyl, and more preferably tertiary butyl, and when $R_4$ or $R_6$ is a phenylalkyl radical, this is preferably benzyl. The phenyl radical of $R_4$ or $R_6$, when either signifies a phenyl, is preferably unsubstituted or substituted with up to 3 substituents selected from 1 or 2 $C_{1-12}$ alkyl radicals and 1 or 2 $C_{1-12}$ alkoxy radicals, the aggregate of the carbon atoms in these substituents not exceeding 12; more preferably unsubstituted or substituted with a $C_{1-4}$ alkyl or $C_{1-4}$ alkoxy radical; and most preferably unsubstituted or substituted with a $C_{1-4}$ alkyl radical. In the case where $R_4$ forms with —NR$_6$— and optionally with a further hetero atom a saturated 5- or 6-membered heterocyclic ring, such heterocyclic ring is preferably a 5- or 6-membered ring optionally with an oxygen or sulphur atom or an —NH group in the 3- or 4-positiion, respectively, and more preferably a piperidine or morpholine ring. $R_5$, when signifying an unsubstituted or substituted phenyl radical, is preferably the former, and $m$ is preferably 2 or 3. When $R_4$, $R_5$ or $R_6$ is or contains an alkyl or alkoxy radical, this is preferably of 1 to 4 carbon atoms, and any cycloalkyl radical as signified or contained by $R_2$, $R_4$, $R_5$ or $R_6$ is preferably cyclopentyl or cyclohexyl.

Of the compounds of formula I, a preferred class is constituted by those of formula Ia,

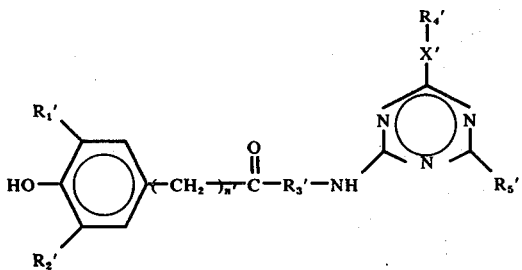

in which
R₁' is a C₄₋₆ tertiary alkyl radical,
R₂' is a C₁₋₈ alkyl radical,
n' is 0 or an integer 1 or 2,
R₃' is —NH— or —O—(CH₂)ₘ'—
wherein m' is an integer 2 or 3,
X' is —O—, —S— or NR₆'—,
  wherein R₆' is a hydrogen atom or a C₁₋₁₈ alkyl, C₅₋₁₂ cycloalkyl, C₆₋₁₂ cycloalkylalkyl, C₇₋₁₂ phenylalkyl or phenyl radical, the latter being unsubstituted or substituted with up to 3 substituents selected from 1 or 2 C₁₋₁₂ alkyl and 1 or 2 C₁₋₁₂ alkoxy radicals, the aggregate of the carbon atoms in these substituents not exceeding 22,
R₄' is, independently, one of the radicals signified by R₆', or, when X' is —NH—, additionally a radical of formula IIa,

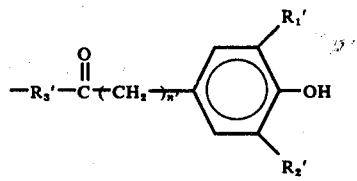

wherein R₁', R₂', n' and R₃' are, independently, as defined above,
or R₄', together with R₆' and the common nitrogen atom, and optionally with an oxygen or sulphur atom or an —NH— group in the 3- or 4-position, form a saturated 5- or 6-membered heterocyclic ring, respectively,
and R₅' is, independently, one of the radicals signified by —X—R₄', or a C₁₋₁₂ alkyl or a phenyl radical.

Of the compounds of formula Ia, a preferred class is constituted by those of formula Ib,

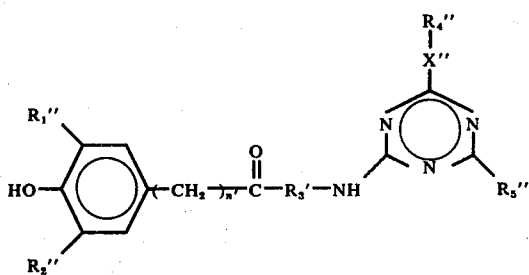

in which
R₁'' and R₂'' are each a tertiary butyl radical,
n' is 0 or an integer 1 or 2,
R₃' is —NH— or —O—(CH₂)ₘ'—
wherein m' is an integer 2 or 3,
X'' is —S— or —NR₆''—, wherein R₆'' is a hydrogen atom or a C₁₋₁₈ alkyl, benzyl or phenyl radical, the latter being unsubstituted or substituted with a C₁₋₄ alkyl or C₁₋₄ alkoxy radical,
R₄'' is, independently, one of the radicals signified by R₆'', or, when X'' is —NH—, additionally a radical of formula IIb,

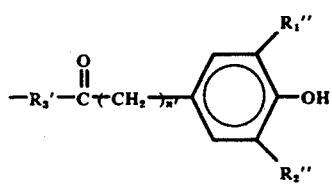

wherein R₁'', R₂'', n' and R₃' are, independently, as defined above,
or R₄'', together with R₆'' and the common nitrogen atom, form a piperidine or morpholine ring,
and R₅'' is, independently, one of the radicals signified by —X''—R₄'', with the proviso that the molecule contains a maximum of 2 radicals or formula IIb.

Of the compounds of formula Ib, a preferred class is constituted by those of formula Ic,

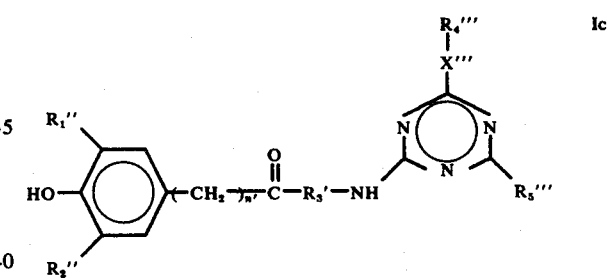

in which
R₁'', R₂'', n' and R₃' and are defined above,
X''' is —NR₆'''—,
  wherein R₆''' is a hydrogen atom or a C₁₋₁₈ alkyl or phenyl radical, the latter being unsubstituted or substituted with a C₁₋₄ alkyl radical,
R₄''' is, independently, one of the radicals signified by R₆''',
or R₄''', together with R₆''' and the common nitrogen atom, form a piperidine or morpholine ring,
and R₅''' is, independently, one of the radicals signified by —X'''—R₄'''.

The invention further provides a process for the production of a compound of formula I, which comprises
a. reacting a compound of formula III,

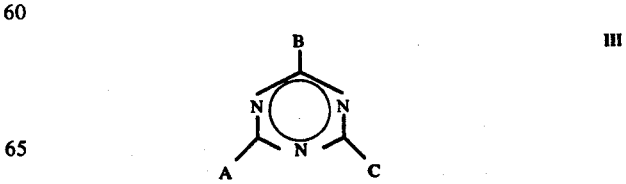

in which A is halogen or a radical of formula IV,

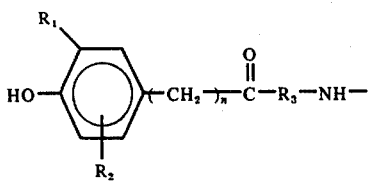

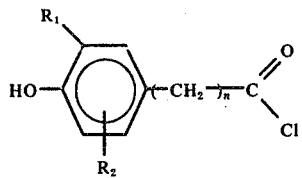

wherein
$R_1$, $R_2$, $n$ and $R_3$ are as defined above,
B is halogen or a radical of formula $-X-R_4$, as defined above,
and C is halogen or a radical $R_5$, as defined above, at least one of A, B and C being halogen,
with a compound of formula V, $$R_4 - X - M \qquad V$$

in which
$R_4$ and X are as defined above,
and M is hydrogen, sodium, potassium or ammonium, with the provisos that when X is $-NR_6-$, M can only be hydrogen, in which case, when $R_6$ is hydrogen and $R_4$ is a radical of formula II, as defined above, $R_3$ therein is only $-NH-$, at least one of A, B, C and $R_4-X-$ being a radical of formula IV, as defined above; or b. reacting a compound of formula VI,

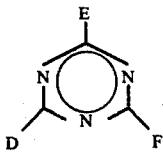

in which
D is $-NH-R_3-H$, wherein $R_3$ is as defined above, or a radical or formula IV, as defined above,
E is $-NH-R_3-H$, wherein $R_3$ is as defined above, or a radical of formula $R_4-X-$, as defined above,
and F is $-NH-R_3-H$, wherein $R_3$ is as defined above, or a radical $R_5$, as defined above,
at least one of D, E and F being $-NH-R_3-H$, with a compound of formula VII,

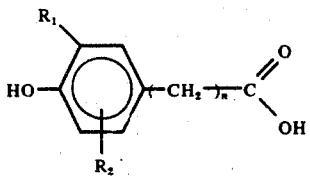

in which $R_1$, $R_2$ and $n$ are as defined above, or a functional derivative thereof.

In the process variant (a), the preferred significance of M when other than hydrogen is sodium. Examples of functional derivatives of the compounds of formula VII are esters, e.g. $C_{1-4}$ alkyl esters, and halides thereof. The preferred functional derivative is the chloride.

A preferred process according to the present invention comprises using in process variant (a) a compound of formula III in which A is a radical of formula IV, or using in process variant (b) the acid chloride of the compound of formula VII, i.e. a compound of formula VIIa, in which $R_1$, $R_2$ and $n$ are as defined above.

In the process of the present invention, whenever hydrogen halide is eliminated, i.e. when a compound of formula III is reacted with one of formula V in which M is hydrogen, or VI with an acid halide of a compound of formula VII, i.e. a compound of formula VIIa, the reaction is preferably effected in a reaction-inert solvent, e.g. benzene, toluene, xylene or dioxan, in the presence of a base, e.g. triethylamine, pyridine, sodium becarbonate, sodium carbonate or sodium hydroxide. When the reagent of formula V in which M is sodium or potassium is used, the reaction likewise is preferably effected in a reaction-inert solvent, such as one of those mentioned above, but the presence of a base is not necessary. Analogous reactions to those just described are reported, for example, in the Journal of the American Chemical Society, 73, 2986 (1951).

When a compound of formula VII or a functional derivative thereof is used and the $-NH-R_3-H$ radical (s) of the compound of formula VI with which it interacts is/are hydrazinyl, i.e. $R_3$ is $-NH-$, the reaction is effected preferably in one of the above-mentioned solvents at a temperature in the range 100° to 160° C, more preferably 120° to 140° C, and in the presence of a catalytic amount of acid, e.g. phosphoric or sulphuric acid. The reaction between a compound of formula VII, or a functional derivative thereof, and a compound of the formula VI containing one or more $-NH-R_3-H$ radicals, in which $R_3$ is $-O-(CH_2)_m$, may be carried out in a similar manner to the analogous reaction described in Houben-Weyl, Volume 8, page 516.

The intermediates of formulae III, V, VI and VII, and the functional derivatives of the latter compound, may be produced in known manner from readily available starting materials, e.g. from trihalo or triaminated triazines using the reactions as described above in process variants (a) and (b).

The present invention further provides a method of stabilizing an organic material against the degradative effects of oxygen, heat and/or light comprising treating the organic material with a compound of formula I, as hereinbefore defined. By the term "treating", as used herein, is meant either incorporating into the body of the organic material susceptible to the degradative effects of oxygen, heat and/or light, or surface coating such organic material, in a manner known per se. The compounds of formula I have stabilizing properties towards the organic materials in which they are incorporated or upon which they form a protective surface coating. In particular, the compounds of formula I in which $n$ is an integer 1 to 3 exhibit more notably antioxidative effects and are thus more suitable for stabilizing organic materials against oxidation in air, whereas those in which $n$ is 0, having more notably ultra-violet absorbing effects, are more suitable for stabilizing organic materials against light, and in particular, ultra-violet light.

Suitable organic materials which benefit from the method of the present invention include such natural substances as rubber, cellulose, wool and silk, and plastics materials, in particular polyolefins, e.g. polyethylene and polypropylene, polyesters, polyacrylic esters, e.g. polymethyl methacrylates, polyphenylene oxides, polyurethanes, polystyrene, polycarbonates, acrylonitrile-butadiene-styrene (ABS) terpolymers, polyamides and especially nylon, polypropylene oxide, polyacrylonitrile and copolymers of the aforementioned polymers. The compounds of the present invention are especially suitable for stabilizing polypropylene, polyethylene, polyesters, polyamides, polyurethanes, polyacrylonitrile, polycarbonates, ABS terpolymers, acrylic ester-styrene-acrylonitrile terpolymers, styrene-acrylonitrile copolymers and styrene-butadiene copolymers.

According to an embodiment of the method of the present invention, the compound of formula I is intimately mixed with the organic material, e.g. a plastics material such as polypropylene, preferably in particulate form, in a kneader or other suitable mixing device, to obtain uniform distribution of the compound throughout the substrate. Such a uniform distribution is often advantageous for good protection of the organic material. The treated material may thereafter be formed into final shape, e.g. by extrusion to form, inter alia, films, tubings or filament. The treated filaments may be made up into textile materials with stability against the degradative effects of oxygen, heat and/or light.

According to a second embodiment of the method of the present invention, particularly suited to stabilization of polymeric or copolymeric materials, the compound of formula I is mixed with the appropriate monomer (s) and/or prepolymer (s) before polymerization or copolymerization is effected. After polymerization or copolymerization, the product has the compound uniformly distributed therethrough. The polymer or copolymer may thereafter be extruded, moulded or otherwise formed into final shape.

The organic materials may also be treated with other additives besides the compounds of formula I to improve their properties, e.g. other stabilizers or co-stabilizers against the degradative effects of oxygen, heat and/or light. In particular, such further additives include 2-hydroxy-benzophenone, organic compounds of sulphur, tin and trivalent phosphorus, and nickel salts of carboxylic acids.

The amount of stabilizing compound of formula I employed in the method of the present invention will naturally depend on several factors, including the mode of application, the particular compound employed and the nature of the organic material to be treated. Thus, for example, when the mode of application is the incorporation of the compound into the body of the organic material, satisfactory results are generally obtained when the amount of compound employed is in the range 0.01 to 5%, preferably 0.05 to 1%, of the weight of the organic material to be treated.

The present invention further provides an organic material whenever treated according to the method of the present invention. Stabilized organic materials according to the invention may exist in solid forms, e.g. foam plastics, sheets such as paper, rods, coatings, foils, films, fibres, granules and powders, or in liquid form, e.g. solutions, emulsions and dispersions such as polishes, creams, paints and lotions, whether opaque, clear or translucent.

The present invention is illustrated by the following Examples, in which the parts and percentages are by weight. The indicated structures of the compounds were determined by microanalysis and inra-red spectroscopy.

EXAMPLE 1

A solution of 4.4 parts of 3-(3,5-di-tert.-butyl-4-hydroxyphenyl)-propionyl chloride is added to a solution of 4 parts of 2-hydrazino-4,6-dimorpholino-1,3,5-triazine, 2 parts of triethylamine and 40 parts of dioxan. The whole is heated to 70° C over the course of 2 hours, after which the precipitate which forms is filtered off, the filtrate is concentrated under vacuum and the residue is recrystallised from methanol. White crystals with a melting point of 202°–203° C and of the formula

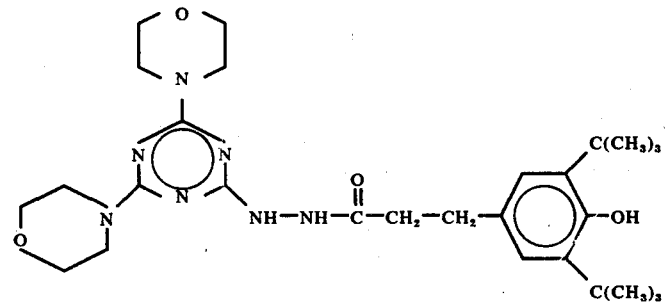

are obtained.

EXAMPLE 2

A solution of 5.7 parts of 4-hydroxy-3,5-di-tert.-butyl-benzoyl chloride is added to a solution of 6 parts of 2-hydrazino-4,6-dipiperadino-1,3,5-triazine, 3 parts of triethylamine and 40 parts of toluene. The whole is heated to 70° C over the course of 2 hours, after which it is cooled to approximately 10° C, the precipitate is filtered off, and the residue is washed, first with water and then with ether. White crystals with a melting point of 256°–259° C and of the formula

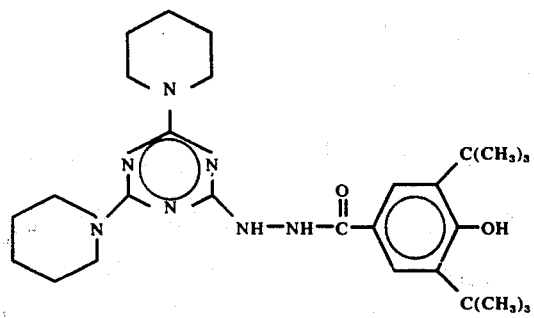

are obtained. The compounds shown below in Examples 3-7 are produced in a similar way.

EXAMPLE 3
Melting point: 205°-206° C

EXAMPLE 4
White crystals Melting point: 150°-152° C

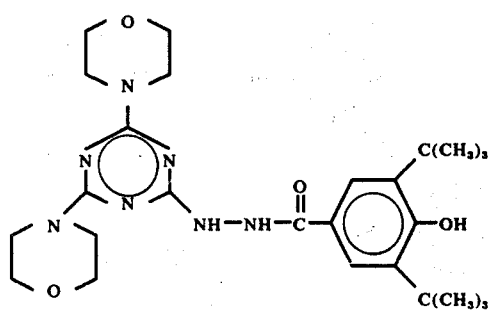

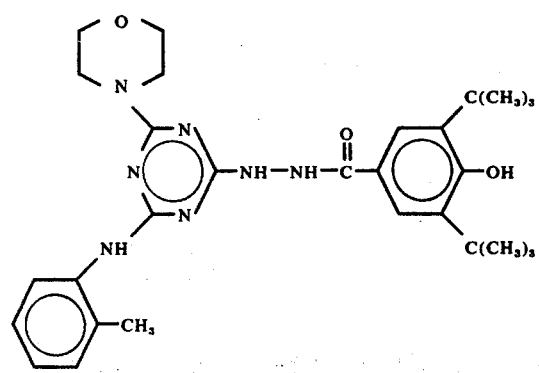

EXAMPLE 5
beige crystals Melting point: 150°-153°

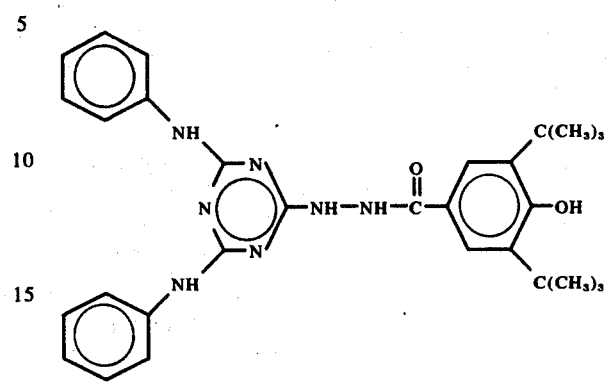

EXAMPLE 6
light yellow resin

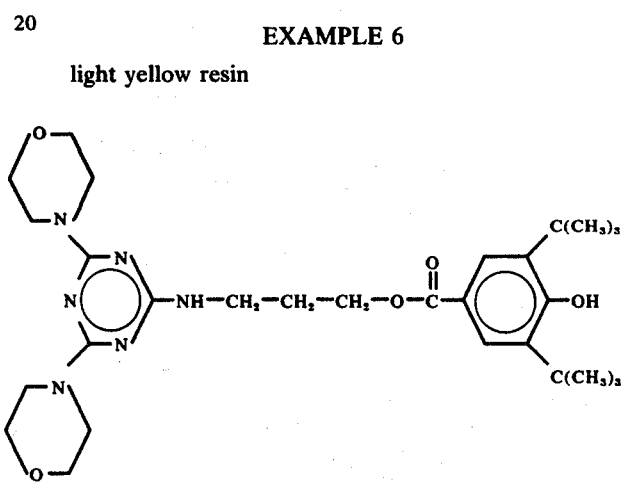

EXAMPLE 7
light yellow oil

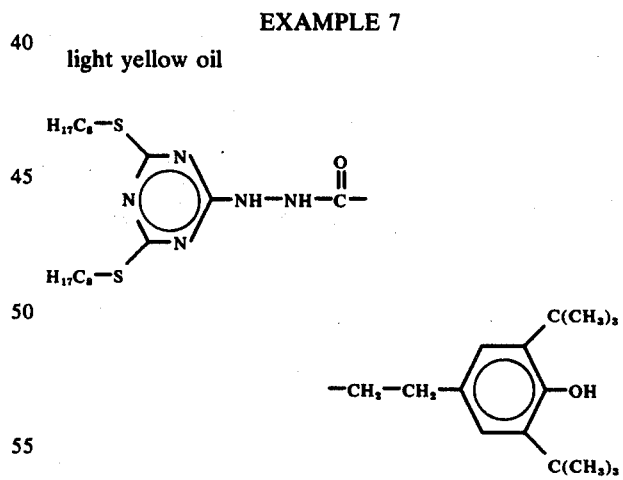

EXAMPLES OF APPLICATION
EXAMPLE A

Polypropylene powder is mixed with 0.4% of the compound of Example 1 until a homogeneous mixture is obtained. After kneading on a roller mill for 5 minutes at 180° C, the material is extruded to give a sheet 1 mm thick. To test the resistance to oxidative degradation, discs of 18 mm diameter are punched out of the sheets, and these discs are placed in an oxygen atmosphere in a closed system. They are then heated to 190°

C, whereby an excess pressure of approximately 20 mm of mercury is developed. Oxidation of the plastic results in a drop in pressure. If the stabilizer is effective, the speed at which the pressure drops is slow. The time it takes for the excess pressure to drop to zero is measured, the result indicating that the compound under test has notable anti-oxidative activity.

EXAMPLE B

Polypropylene powder is mixed with 0.4% of the compound of Example 3 until a homogeneous mixture is obtained. After kneading on a roller mill for 5 minutes at 180° C, 1 mm thick sheets are extrusion moulded. To test the resistance to ageing, an accelerated ageing test is carried out at 140° C in an air-circulating oven. In this test too notable results were obtained.

What is claimed is:

1. A compound of the formula

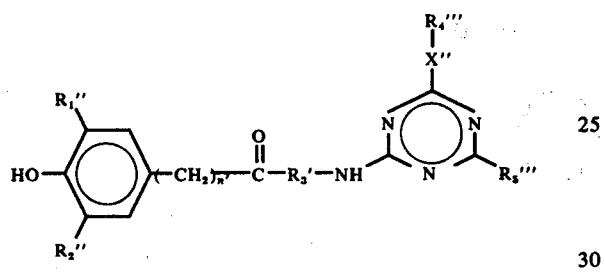

wherein
$R_1''$ and $R_2''$ are each a tertiary butyl radical,
$n'$ is 0 or an integer 1 or 2,
$R_3'$ is —NH— or —O—(CH$_2$)$_{m'}$—
wherein $m'$ is an integer 2 or 3,
$X''$ is —S— or —NR$_6'''$—,
wherein $R_6'''$ is hydrogen, $C_1-_{18}$ alkyl, unsubstituted phenyl or phenyl monosubstituted by $C_1-_4$ alkyl,
$R_4'''$ is, independently, one of the significances of $R_6'''$,
or $R_4'''$, together with $R_6'''$ and the common nitrogen atom, form a piperidine or morpholine ring, and
$R_5'''$ is, independently, one of the significances of —X''—R$_4'''$.

2. A compound according to claim 1, of the formula,

4. A compound according to claim 1, of the formula,

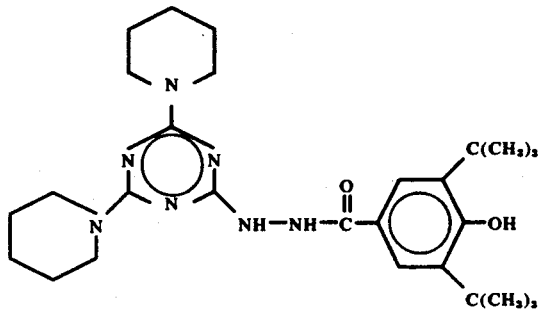

5. A compound according to claim 1, of the formula,

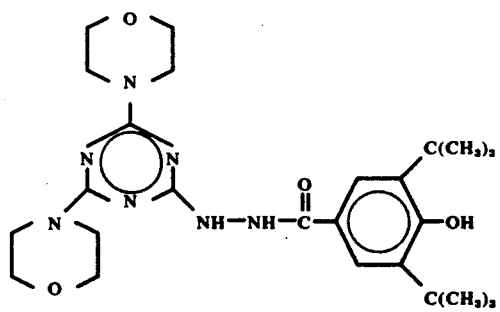

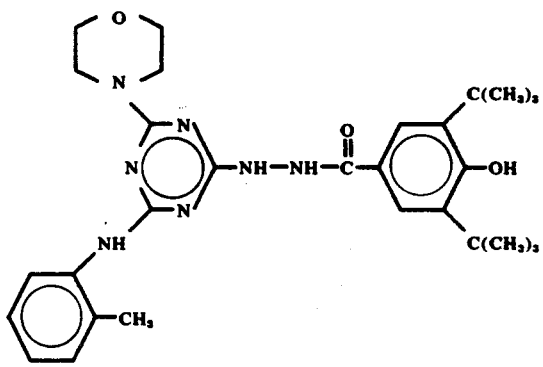

3. A compound according to claim 1, of the formula,

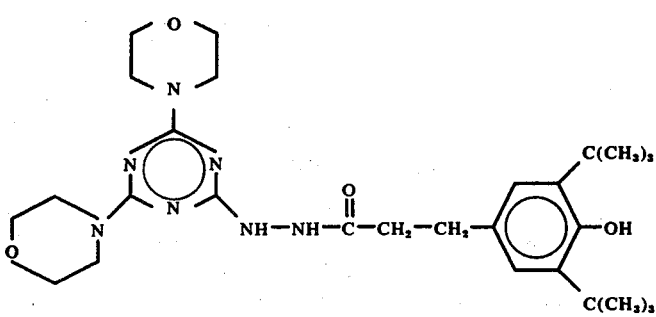

6. A compound according to claim 1, of the formula,

7. A compound according to claim 1, of the formula,
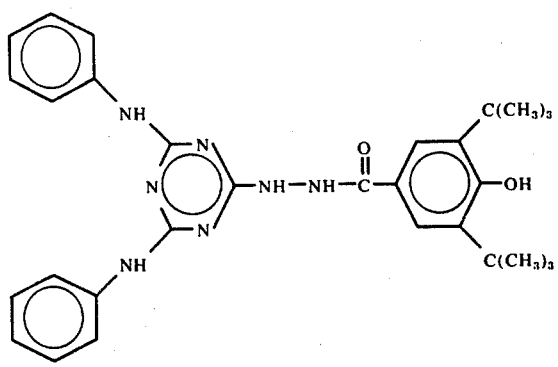
8. A compound according to claim 1, of the formula,
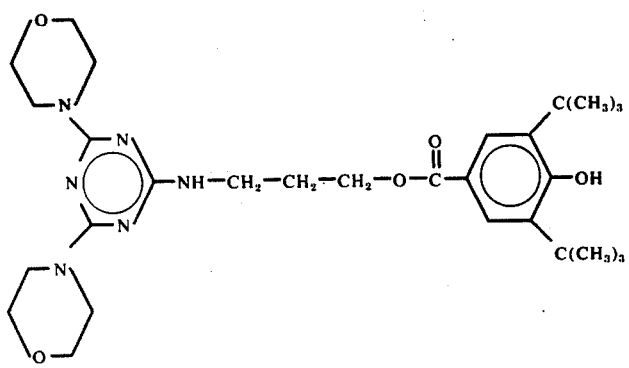
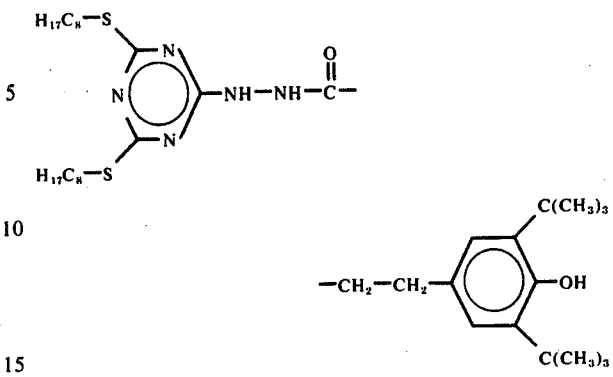
9. A compound according to claim 1 wherein $X''$ is $-NR_6'''$.
10. A compound according to claim 1 wherein $R_3'$ is $-NH-$.
* * * * *